(12) United States Patent
Suriye et al.

(10) Patent No.: US 9,765,264 B2
(45) Date of Patent: Sep. 19, 2017

(54) PROCESS FOR REDUCING THE BROMINE INDEX OF A HYDROCARBON

(75) Inventors: Kongkiat Suriye, Samutprakan (TH); Surachate Chalothorn, Bangkok (TH); Nakarin Mongkolsiri, Nonthaburi (TH); Wiroon Tanthapanichakoon, Bangkok (TH)

(73) Assignee: SCG Chemicals Co., Ltd., Bangkok (TH)

( * ) Notice: Subject to any disclaimer, the term of this patent is extended or adjusted under 35 U.S.C. 154(b) by 1490 days.

(21) Appl. No.: 13/518,751

(22) PCT Filed: Dec. 24, 2009

(86) PCT No.: PCT/TH2009/000001
§ 371 (c)(1),
(2), (4) Date: Jun. 22, 2012

(87) PCT Pub. No.: WO2011/078810
PCT Pub. Date: Jun. 30, 2011

(65) Prior Publication Data
US 2013/0006032 A1    Jan. 3, 2013

(51) Int. Cl.
*C10G 25/03*    (2006.01)
*B01J 20/18*    (2006.01)
*C07C 7/13*    (2006.01)
*B01J 20/28*    (2006.01)

(52) U.S. Cl.
CPC .............. *C10G 25/03* (2013.01); *B01J 20/18* (2013.01); *B01J 20/2808* (2013.01); *C07C 7/13* (2013.01); *C10G 2300/1096* (2013.01); *C10G 2300/4018* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,346,609 A | 9/1994 | Fletcher et al. | |
| 7,744,750 B2 * | 6/2010 | Brown | C07C 7/13 208/263 |
| 2001/0045376 A1 | 11/2001 | Brown et al. | |
| 2006/0020154 A1 | 1/2006 | Lo et al. | |
| 2006/0270886 A1 * | 11/2006 | Brown | C10G 25/003 585/829 |
| 2007/0112239 A1 | 5/2007 | Brown et al. | |
| 2007/0112240 A1 | 5/2007 | Brown et al. | |
| 2007/0129235 A1 | 6/2007 | Brown et al. | |

(Continued)

OTHER PUBLICATIONS

Chen et al., "Study on several mesoporous materials catalysts applied to the removal of trace olefins from aromatics and commercial sidestream tests," *Industrial and Engineering Chemistry Research* 48(23):10359-10363, Sep. 28, 2009.

(Continued)

Primary Examiner — Tam M Nguyen
(74) Attorney, Agent, or Firm — Seed IP Law Group LLP (57) ABSTRACT

A process for reducing the bromine index (BI) of a hydrocarbon feedstock, for example an aromatic hydrocarbon feedstock. Removal of contaminants, more specifically bromine-reactive contaminants such as unsaturated hydrocarbons (e.g., olefins) cause the reduction in the bromine index (BI) of the hydrocarbon feedstock. The process involves providing an adsorbent, such as a zeolite.

34 Claims, 5 Drawing Sheets

(56) References Cited

U.S. PATENT DOCUMENTS

| | | | |
|---|---|---|---|
| 2008/0194898 A1* | 8/2008 | Sohn | C07C 6/126 585/470 |
| 2013/0006032 A1* | 1/2013 | Suriye | C07C 7/13 585/824 |

OTHER PUBLICATIONS

International Search Report, mailed Apr. 7, 2011, for PCT/TH2009/000001, 6 Pages.

* cited by examiner

PROCESS FOR REDUCING THE BROMINE INDEX OF A HYDROCARBON

BACKGROUND

Technical Field

The present disclosure relates generally to the processing or purifying of hydrocarbon feedstocks. More specifically, the present disclosure relates to a process for reducing a bromine index of a hydrocarbon feedstock, for example an aromatic hydrocarbon feedstock, via an adsorption process or technique.

Description of the Related Art

Hydrocarbon feedstocks, for example aromatic hydrocarbon feedstocks, are commonly derived from various petrochemical processes such as naphtha reforming and thermal cracking (pyrolysis). Aromatic hydrocarbon feedstocks are commonly used in a variety of petrochemical and industrial processes. For example, aromatic hydrocarbon feedstocks that contain benzene, toluene, and xylene (BTX), and heavy aromatic streams (e.g., with hydrocarbons having at least 9 carbon atoms), are often used in the production of para-xylene.

However, aromatic hydrocarbon feedstocks often contain contaminants, for instance bromine-reactive compounds such as unsaturated hydrocarbons (e.g., olefins such as mono-olefins and multi-olefins, diolefins, and styrenes), which can cause undesirable side reactions in downstream processes. Traces of olefins can also form gums and undesirable byproducts, which can coat the heat transfer surfaces of reaction or operating systems, and hence reduce the efficiency of said reaction or operating systems.

Accordingly, said contaminants should be removed from the aromatic hydrocarbon feedstocks before the aromatic hydrocarbon feedstocks are used for the various petrochemical and industrial processes.

A conventional method for measuring levels of unsaturation or contamination of hydrocarbons, for example aromatic hydrocarbons, is via the bromine index (BI). Typically, the bromine index (BI) of an aromatic hydrocarbon reflects the level of unsaturation, and hence contamination, of the aromatic hydrocarbon. The measurement of the bromine index (BI) in an aromatic hydrocarbon can be done via the method described by ASTM D 5776-99, the entire contents of which are incorporated herein by reference. Specifically, the bromine index (BI) is defined as the number of milligrams of bromine consumed by 100 grams of hydrocarbon sample under the required conditions. This is to say, the bromine index (BI) of a hydrocarbon sample can be defined as the number of milligrams of bromine that will react with unsaturated hydrocarbons (e.g., olefins) that are present in 100 grams of said hydrocarbon sample.

There are numerous existing methods or techniques for reducing the bromine index (BI) of hydrocarbon feedstocks (e.g., aromatic hydrocarbons feedstocks). Removal of unsaturated hydrocarbons, for example olefins, from aromatic hydrocarbon feedstock has been commercially performed using alkylation, polymerization, and oligomerization processes, which are catalyzed by hydrotreating catalysts and/or acid clay catalysts. The alkylation, polymerization, and oligomerization processes typically require multiple processing units or equipment units, for example a catalytic unit for the alkylation, polymerization, and oligomerization processes, and a separation unit for the distillation or extraction of formed products. Accordingly, with such existing processes, capital investment to build or obtain the multiple processing units or equipment units is required.

Said catalysis occurs between the unsaturated hydrocarbon molecule (e.g., olefin molecule) and the catalyst (e.g., clay catalyst), and results in formation of heavy molecule hydrocarbons as a by-product. Accordingly, processes for removing said heavy molecule hydrocarbon by-products are required before further fractionation, processing, or utilization of the aromatic hydrocarbon feedstock.

In addition, due to the formation of heavy molecule hydrocarbons, used catalysts generally have to be regenerated with oxidative agents for removing coke. This regeneration process is described in United States patent applications of publication numbers US 20060270886 and US 20070112240. For ensuring complete coke removal, said regeneration process has to be performed at a significantly high temperature. Furthermore, a rejuvenation process using a reductive or reducing agent is typically required. The need for high temperatures during the regeneration and rejuvenating processes adds to the overall or total costs associated with existing processes for removing contaminants such as unsaturated hydrocarbons from aromatic hydrocarbon feedstocks.

More recently, zeolites have been proposed as replacement for clays in the removal of bromine reactive contaminants such as unsaturated hydrocarbons (e.g., olefins) from aromatic hydrocarbon feedstocks. Methods or techniques for removing bromine reactive contaminants from aromatic hydrocarbon feedstocks with the use of zeolites have been disclosed and described in several patent documents.

For example, U.S. Pat. No. 6,368,496 discloses a method for removing bromine reactive contaminants from an aromatic hydrocarbon stream, the method including contacting the aromatic hydrocarbon stream with an acid-active catalyst composition under specific pressure and temperature conditions. U.S. Pat. No. 6,781,023 discloses a catalytic method for removing bromine reactive contaminants from an aromatic hydrocarbon stream, the method comprising providing the aromatic hydrocarbon feedstream and contacting the feedstream with an unbound or self-bound MCM-22 under specific pressure and temperature conditions.

In most industries, including the petrochemical and chemical industries, profit margins and safety are important considerations. Accordingly, there remains a need for alternative, for instance, more cost-effective, safer, and/or efficient methods and techniques for removing contaminants, for example bromine-reactive contaminants such as unsaturated hydrocarbons, from hydrocarbon feedstocks or aromatic hydrocarbon feedstocks, and correspondingly reducing the bromine index (BI) of said hydrocarbon feedstocks or aromatic hydrocarbon feedstocks.

BRIEF SUMMARY

In accordance with a first aspect of the present disclosure, there is disclosed a process for reducing the bromine index (BI) of a hydrocarbon feedstock. The process includes contacting the hydrocarbon feedstock with an adsorbent comprising a zeolite with a pore size of between approximately 4 Å and 8 Å in an adsorption process so as to reduce the bromine index (BI) of the hydrocarbon feedstock.

In accordance with a second aspect of the present disclosure, there is disclosed a method for reducing a bromine index (BI) of an aromatic hydrocarbon. The method includes providing an adsorbent, the adsorbent comprising a zeolite. The zeolite includes pores with a pore size of between approximately 4 Å and 8 Å. The method further includes contacting an aromatic hydrocarbon feedstock with the zeolite, the aromatic hydrocarbon feedstock including unsaturated hydrocarbons, and adsorbing at least a portion of the unsaturated hydrocarbons within the pores of the zeolite in an adsorption process. In addition, the method includes bringing inert gas into contact with the zeolite, wherein the inert gas one of facilitates and effectuates removal of the adsorbed unsaturated hydrocarbons within the pores of the zeolite therefrom to thereby one of facilitate and effectuate regeneration of the zeolite.

In accordance with a third aspect of the present disclosure, there is disclosed a system for reducing a bromine index (BI) of an aromatic hydrocarbon feedstock. The system includes a housing within which an adsorbent can be retained. The adsorbent includes a zeolite with pores of a pore size of between approximately 4 Å and 8 Å. The system further includes an inlet coupled to the housing through which the aromatic hydrocarbon feedstock can pass to contact the adsorbent, the aromatic hydrocarbon feedstock including unsaturated hydrocarbon. At least a portion of the unsaturated hydrocarbons can be adsorbed within the pores of the zeolite. The system also includes a gas inlet coupled to the housing to bring a substantially inert gas into contact with the adsorbent so as to remove the unsaturated hydrocarbons from the pores of the zeolite. Furthermore, the system includes an outlet coupled to the housing to carry unsaturated hydrocarbon removed from the pores of the zeolite by the inert gas.

In accordance with a fourth aspect of the present disclosure, there is disclosed a process for reducing a bromine index (BI) of a hydrocarbon feedstock. The process includes providing an adsorbent, the adsorbent including a zeolite with pores of a pore size of between approximately 4 Å and 8 Å. The process further includes contacting the hydrocarbon feedstock with the zeolite, the hydrocarbon feedstock comprising contaminants. The contacting of the hydrocarbon feedstock with the zeolite one of facilitates and effectuates reduction of the bromine index (BI) of the hydrocarbon feedstock. At least 60% of the bromine index (BI) reduction results from adsorbing the contaminants of the hydrocarbon feedstock within the pores of the zeolite via an adsorption process.

BRIEF DESCRIPTION OF THE SEVERAL VIEWS OF THE DRAWINGS

Embodiments of the present disclosure are described hereinafter with reference to the figures, in which.

DETAILED DESCRIPTION

It is often important to remove contaminants, for example bromine-reactive contaminants such as unsaturated hydrocarbons (e.g., olefins, diolefins, and styrenes), from hydrocarbons or hydrocarbon feedstocks (e.g., aromatic hydrocarbon feedstocks). This is because the presence of said contaminants in aromatic hydrocarbon feedstocks can cause undesirable side reactions in downstream processes utilizing said aromatic hydrocarbons feedstocks. Generally, the level or amount of bromine-reactive contaminants in aromatic hydrocarbon feedstocks corresponds with the bromine index (BI) of said aromatic hydrocarbon feedstocks. It is generally important to reduce the bromine index (BI) of aromatic hydrocarbons. The drive for increased profit margins and/or safety in industry produces a continual demand for more cost-effective, safer, and/or efficient methods, processes, and/or techniques for removing bromine-reactive contaminants such as unsaturated hydrocarbons (e.g., olefins, diolefins, and styrenes) from aromatic hydrocarbon feedstocks, and correspondingly reducing the bromine index (BI) of said aromatic hydrocarbon feedstocks.

Embodiments of the present disclosure relate to methods, processes, techniques, systems, devices, and/or components for reducing the bromine index (BI) of a hydrocarbon (also referred to as a hydrocarbon feed, hydrocarbon feedstock, or hydrocarbon feedstream). More specifically, many embodiments relate to methods, processes, techniques, systems, devices, and/or components for reducing the bromine index (BI) of an aromatic hydrocarbon (also referred to as an aromatic hydrocarbon feed, aromatic hydrocarbon feedstock, or aromatic hydrocarbon feedstream).

Generally, the bromine index (BI) of a hydrocarbon (e.g., an aromatic hydrocarbon) corresponds to, is correlated with, or reflects, the level or amount of contaminants, more specifically bromine-reactive contaminants within the hydrocarbon. For purposes of the present disclosure, bromine-reactive contaminants can be understood to include unsaturated hydrocarbons such as olefins (e.g., mono-olefins and multi-olefins), diolefins, and styrenes. However, a person of ordinary skill in the art will understand that contaminants, more specifically bromine-reactive contaminants, can further include other organic compounds, for example other types of unsaturated hydrocarbons, that may unadvantageously affect the function, reactivity, structure, and/or use of a hydrocarbon.

Most embodiments of the present disclosure relate to methods, processes, techniques, systems, devices, and/or components for removing bromine-reactive contaminants from a hydrocarbon. More specifically, many embodiments relate to methods, processes, techniques, systems, devices, and components for removing bromine-reactive contaminants from an aromatic hydrocarbon.

Hydrocarbon/Aromatic Hydrocarbon Feed, Feedstock, or Feedstream

The term "feed", "feedstock", or "feedstream" used in the present disclosure refers to hydrocarbons, for example aromatic hydrocarbons, before contact with an adsorbent. In most embodiments of the present disclosure, the adsorbent includes a molecular sieve, more specifically a zeolite. The terms "feed", "feedstock", and "feedstream" can be used interchangeably.

Hydrocarbon feedstocks can be obtained or extracted via numerous existing petrochemical processes that are known to a person of ordinary skill in the art. Examples of hydrocarbon (e.g., aromatic hydrocarbon) extraction processes are described in the Handbook of Petroleum Processing, McGraw-Hill, New York 1996, p. 2.13-2.22.

For instance, hydrocarbon feedstocks (e.g., aromatic hydrocarbon feedstocks) can be obtained from reforming and cracking processes. For example, aromatic hydrocarbon feedstocks can be obtained from the cracking of naphtha. In addition, aromatic hydrocarbons, for example benzene, toluene, xylene, ethylbenzene, and cumene, can be derived from reformates.

The aromatic hydrocarbon feedstock of many embodiments of the present disclosure includes mainly benzene, toluene, and xylene. In addition, the aromatic hydrocarbon feedstock can further include benzene-reactive compounds or contaminants, for example unsaturated hydrocarbons such as olefins (e.g., mono-olefins and multi-olefins), diolefins, and styrenes.

The term "mono-olefins" as used in the present disclosure refers to olefinic compounds containing one carbon-carbon double bond per molecule. Examples of mono-olefins include ethylene, propylene, butenes, hexenes, and octenes. The term "multi-olefins" as used in the present disclosure refers to olefinic compounds containing at least two carbon-carbon double bonds per molecule. Examples of multi-olefins are butadienes, cyclopentadienes and isoprenes.

In most embodiments of the present disclosure, the aromatic hydrocarbon feedstock has a bromine index (BI) of less than 500 (i.e., less than 500 mg of bromine/100 g of the aromatic hydrocarbon feedstock sample). In some embodiments, the aromatic hydrocarbon feedstock has a bromine index (BI) of less than 250 (i.e., less than 250 mg of bromine/100 g of the aromatic hydrocarbon feedstock sample). In selected embodiments, the aromatic hydrocarbon feedstock has a bromine index (BI) of less than 100 (i.e., less than 100 mg of bromine/100 g of the aromatic hydrocarbon feedstock sample). In specific embodiments, the aromatic hydrocarbon feedstock has a bromine index (BI) of less than 50 (i.e., less than 50 mg of bromine/100 g of the aromatic hydrocarbon feedstock sample).

The bromine index (BI) of the aromatic hydrocarbon feedstock is reduced after performance of processes provided by embodiments of the present disclosure. This is to say, bromine-reactive contaminants such as unsaturated hydrocarbons are removed from the aromatic hydrocarbon feedstock by performance of particular processes provided by embodiments of the present disclosure. In most embodiments of the present disclosure, an adsorbent is used for adsorbing, and hence removing, the bromine-reactive contaminants from the aromatic hydrocarbon feedstock.

Adsorbent (Zeolite)

In the following discussion, embodiments using zeolite(s) as an adsorbent, or part of an adsorbent, are sometimes described. It will be understood that in such described embodiments, "zeolite" can be replaced by "adsorbent".

An adsorbent is used in most embodiments of the present disclosure for adsorbing, and hence removing, bromine-reactive contaminants such as unsaturated hydrocarbons from aromatic hydrocarbon feedstocks.

In many embodiments, the adsorbent is loaded onto or within an adsorber (also known as an adsorber column or an adsorber system, or simply "support"). In most embodiments, the adsorbent includes a zeolite.

Zeolites are three-dimensional, microporous, crystalline solids with well-defined structures that generally include aluminum, silicon, and oxygen atoms in a regular framework. The silicon and aluminum atoms are typically tetrahedrally coordinated with each other through shared oxygen atoms. The substantially porous structure of zeolites allows for accommodation of a wide variety of molecular and ionic species, for example, positively charged ions (i.e., cations) such as metal ions (e.g., $Na^+$, $K^+$, $Ca^{2+}$, and $Mg^{2+}$), water, and other molecules.

There are naturally occurring zeolites as well as synthetic zeolites. Naturally occurring zeolites are rarely pure, and tend to be contaminated to varying degrees by other minerals, metals, quartz, or other zeolites. For this reason, naturally occurring zeolites are generally excluded from many commercial applications where uniformity and purity are essential. Synthetic zeolites are widely used in industry (or commercially). Generally, synthetic zeolites have a regular and reproducible structure, and can hence behave in a predictable manner.

The zeolites used with most embodiments of the present disclosure function as molecular sieves or molecular sieve systems.

Molecular sieves are structures that are capable of selectively sorting molecules based primarily on the sizes of said molecules. This is generally because of the very regular pore structure and/or size of a particular zeolite. The size or dimensions of a particular zeolite's pores controls or determines the maximum size of the molecular and/or ionic species that can enter, pass through, and/or be adsorbed or retained within, the particular zeolite's pores.

Zeolites used with embodiments of the present disclosure are specifically selected for their particular morphology, porosity, pore size, pore size distribution, and/or surface properties. For example, the zeolite used in particular embodiments, is selected for allowing selective entry or access to particular molecular species (e.g., unsaturated hydrocarbons such as olefins) while preventing entry or access to other molecular species (e.g., aromatic hydrocarbon).

In many embodiments, the zeolite has a pore size of between approximately 4 Å and 8 Å. In some embodiments, the zeolite has a pore size of between approximately 5 Å and 7 Å. In selected embodiments, the zeolite has a pore size of between approximately 5.5 Å and 6.5 Å.

In most embodiments, the zeolite has a silicon/aluminum (i.e., Si/Al) of between approximately 1 and 150. In many embodiments, the zeolite has a Si/Al of between approximately 2 and 100. In several embodiments, the zeolite has a ratio of Si/Al of approximately 5 to 50. In selected embodiments, the zeolite has a ratio of Si/Al of approximately 10 and 25.

In disclosed embodiments, the zeolite has a surface area of about 50 to about 900 $m^2$/gram and an $Na_2O$ weight % of about 0.0001 to about 10.

Zeolites of many embodiments of the present disclosure are intermediate pore zeolites, and can be naturally occurring or synthetic crystalline molecular sieves. Zeolites and their isotypes, as provided by embodiments of the present disclosure, including those listed below, are described in "Atlas of Zeolite Structure Types", Eds. W. H. Meier, D. H. Olson and Ch. Baerlocher, Elsevier, Fourth Edition, 1996, the contents of which are incorporated herein by reference. Examples of intermediate pore zeolites, as provided by the present disclosure, includes zeolites having the structure type of MFI, MEL, MRE, MTW, EUO, MTT, MFS, AEL, AFP, HEU, FER and TON, as well as any combination thereof.

In some embodiments, the adsorbent includes one zeolite having the structure type of MFI, MEL, MRE, MTW, EUO, MTT, MFS, AEL, AFP, HEU, FER and TON. In other embodiments, the absorbent include more than one, for example, two, three, four, five, or more of zeolite having the structure type of MFI, MEL, MRE, MTW, EUO, MTT, MFS, AEL, AFP, HEU, FER and TON. In selected embodiments, the adsorbent include one zeolite having the structure type of MFI, such as ZSM-5.

In many embodiments, the particular morphology, porosity, pore size, pore size distribution, and/or surface properties of the selected zeolite enables selective adsorption of contaminants (e.g., bromine-reactive contaminants) present with the hydrocarbon feedstock (e.g., the aromatic hydrocarbon feedstock) onto the surface, more specifically within the pores, of said zeolite. In numerous embodiments, the zeolite has a pore size that allows entry of only the contaminants (e.g., the bromine-reactive contaminants such as unsaturated hydrocarbons) and not the aromatic hydrocarbon feedstock.

In many embodiments, the adsorption of the contaminants, for example unsaturated hydrocarbons, of the aromatic hydrocarbon feedstock within the pores of the zeolite occurs during an adsorption process (e.g., a liquid adsorption process or a gas adsorption process).

Adsorption Process

In accordance with most embodiments of the present disclosure, an adsorption process is performed, wherein the hydrocarbon feedstock or aromatic hydrocarbon feedstock contacts the adsorbent, which includes the zeolite, under selected conditions (e.g., pressure, temperature, and weigh hourly space velocity (WHSV)) to thereby remove the contaminants, for example bromine-reactive contaminants such as unsaturated hydrocarbons from said hydrocarbon feedstocks or aromatic hydrocarbon feedstocks.

In many embodiments of the present disclosure, the adsorption process is either a liquid adsorption process or a gas adsorption process. In many embodiments, the adsorption process is performed or carried out at a pressure of between approximately 0.5 bar and 100 bar. In numerous embodiments, the adsorption process is carried out at a pressure of between approximately 1 bar and 50 bar. In some embodiments, the adsorption process is carried out at a pressure of between approximately 5 bar and 40 bar. In selected embodiments, the adsorption process is carried out at a pressure of between approximately 10 bar and 30 bar.

In many embodiments of the present disclosure, the adsorption process (e.g., the liquid phase adsorption process) is performed at a temperature between approximately 10° C. and 120° C. In many embodiments, the adsorption process is performed at a temperature between approximately 20° C. and 110° C. In numerous embodiments, the adsorption process is performed at a temperature between approximately 25° C. and 100° C. In some embodiments, the adsorption process is performed at a temperature between approximately 40° C. and 80° C., for instance between approximately 15° C. and 40° C., or between approximately 20° C. and 40° C.

In most embodiments of the present disclosure, the adsorption process (e.g., the liquid phase adsorption process) is performed at a WHSV of between approximately 0.01 and 250 $hr^{-1}$. In many embodiments, the adsorption process is performed at a WHSV of between approximately 0.1 and 200 $hr^{-1}$. In some embodiments, the adsorption process is performed at a WHSV of between approximately 1 and 100 $hr^{-1}$. The WHSV can be based on the weight of the adsorbent used. The WHSV can be varied depending on the weight of the adsorbent (e.g., zeolite) used.

The performance of the adsorption process (e.g., the liquid phase adsorption process) results in adsorption of contaminants, for example bromine-reactive contaminants such as unsaturated hydrocarbons, on the surface of the zeolite, more specifically within the pores of the zeolites.

Generally, a fresh or regenerated adsorbent (also referred to as a fresh molecular sieve or a fresh adsorbent), such as fresh zeolite, is provided at the start of the adsorption process. This is to say, a regenerated adsorbent, such as a fresh zeolite, is generally used for the process.

For purposes of the present disclosure, the term "fresh zeolite" as used herein refers to a zeolite that has not been exposed to a hydrocarbon feedstock or aromatic hydrocarbon feedstock under the conditions required for the adsorption process as described above for a substantial length of time (e.g., approximately 24 hours), or to a zeolite that has been regenerated such that its function, structure, and/or reactivity is similar to that of said zeolite that has not been exposed to the hydrocarbon feedstock under the conditions for the adsorption process (e.g., the liquid phase adsorption process) for a substantial length of time.

In most embodiments, after the adsorption process (e.g., the liquid phase adsorption process) has occurred for a length of time, more specifically a substantial length of time (e.g., approximately 24 hours), a substantial amount of contaminants, for example unsaturated hydrocarbon molecules, will have be adhered onto the surface of the zeolite, more specifically within the pores of the zeolite. When a substantial amount of contaminants have been adhered onto the surface, more specifically within the pores, of the zeolite, the zeolite can be referred to as a "spent zeolite". This is to say, when a substantial amount of contaminants have been adhered onto the surface, more specifically within the pores, of an adsorbent, the adsorbent can be referred to as a "spent adsorbent".

Typically, a spent zeolite has an altered structure, and loses at least some of its functional (e.g., adsorption) capabilities. A spent zeolite has a substantial percentage of its pores occupied by contaminants (e.g., unsaturated hydrocarbon molecules). Accordingly, a spent zeolite generally has to be replaced with a fresh zeolite or be regenerated (via a regeneration process) to produce a fresh or regenerated zeolite.

For example, in operation of some methods or processes of the present disclosure, a zeolite might reduce the bromine index (BI) of a hydrocarbon feedstock (e.g., an aromatic hydrocarbon feedstock) by at least approximately 30%, at least approximately 40%, at least approximately 50%, at least approximately 60%, at least approximately 70%, at least approximately 80%, or by at least approximately 90%. All or substantially all of this reduction (e.g., at least approximately 20%, 40%, 60%, 80%, 90%, 95%, or even 100%) might be attributable to adsorption of contaminants on the zeolite without chemical modification of the contaminants. A zeolite might be considered "spent" in a given process if it no longer reduces the bromine index (BI) of a hydrocarbon feedstock (e.g., an aromatic hydrocarbon feedstock) by at least approximately 30%, at least approximately 40%, at least approximately 50%, at least approximately 60%, or at least approximately 70% of the reduction the same fresh zeolite provided. For example, if a fresh zeolite reduced bromine index (BI) of a particular hydrocarbon feedstock by at least 50% of the reduction the same fresh zeolite provided in a given process, then it might be considered spent if it no longer reduced bromine index (BI) of a similar hydrocarbon feedstock by 70% of that reduction (that is, if it did not reduce bromine index (BI) of a similar hydrocarbon feedstock by 70% of 50%, namely 35%).

Currently (e.g., as described in prior art documents), regeneration of molecular sieves, for example zeolites, is commonly carried out by using an oxidizing agent for completely oxidizing heavy atoms of hydrocarbons such as coke formed during the alkylation, oligomerization, and polymerization of catalyst. The temperature used for existing regeneration processes is typically relatively high, for example approximately 500° C., in order to completely oxidize all the heavy atoms of hydrocarbons. Such high temperatures can require a significant expenditure of energy resources, and hence increase operating costs.

However, with embodiments of the present disclosure, temperatures required for the regeneration of molecular sieves, for example spent zeolites are relatively lower, for example less than 300° C.

Furthermore, with prior art molecular sieves (and methods or processes for removing contaminants from hydrocarbon feedstocks), additional performance of a rejuvenation process is typically required after performance of a regeneration process. The rejuvenation process utilizes a reductive agent or reducing agent for processing a spent molecular sieve for producing a fresh or regenerated molecular sieve. However, many embodiments of the present disclosure do not require performance of a rejuvenation process (i.e., do not require the use of a reductive agent) for processing a spent molecular sieve for producing a fresh or regenerated molecular sieve.

Regeneration Process

Regeneration processes are provided by many embodiments of the present disclosure for processing or regenerating spent zeolites to produce fresh zeolites.

The regeneration of a spent zeolite generally involves the detachment or removal of adsorbed contaminants, for example bromine-reactive contaminants such as unsaturated hydrocarbons, from the surface, more specifically from the pores, of the zeolite. The detached contaminants can be retrieved or collected, and thereafter disposed of, or further processed, as desired. The detachment or removal of adsorbed contaminants from the surface, more specifically from the pores, of the zeolite, frees or makes available said surface, more specifically said pores, of the zeolite for allowing a subsequent adsorption and removal of contaminants from additional hydrocarbon feedstocks or aromatic hydrocarbon feedstocks that comes into contact with freed surface, more specifically pores, of the zeolite.

In most embodiments, an inert or substantially unreactive gas is used in the regeneration process for regenerating the spent zeolite. In many embodiments, the inert or substantially unreactive gas used is non-hydrocarbon gas such as nitrogen, helium or argon. In some embodiments, the inert gas used is hydrocarbon gas such as methane or ethane gas.

For purposes of the present disclosure, a "substantially unreactive gas" or an "inert gas" refers to a gas whether hydrocarbon or non-hydrocarbon gas or mixture of gases whether hydrocarbon or non-hydrocarbon gas that is not chemically reactive with contaminants (e.g., unsaturated hydrocarbons) or derivatives of the contaminants, which may be adsorbed on the adsorbent (e.g., zeolite). In this disclosure or situation, at least approximately 50%, 60%, 70%, 90%, 95%, or 100% of the removed contaminants can be removed chemically unaltered from the adsorbent using the substantially unreactive gas or the inert gas. For example, the unsubstantially unreactive gas or the inert gas may not contain any substantial amount of an oxidizing agent, which during regeneration may oxidize adsorbed olefins. Similarly, the unsubstantially unreactive gas or the inert gas may not contain any substantial amount of any reducing agent, which may reduce adsorbed olefins. The phrase "not contain any substantial amount" references that the unsubstantially unreactive gas or the inert gas may contain less than approximately 5%, 10%, 15%, 20%, or 25% of oxygen an/or another oxidizing agent (based on volume). For example, the unsubstantially unreactive gas or the inert gas can include at least approximately 70%, 80%, 90%, 95%, 98%, or 99% (or even 100%) nitrogen, helium, argon, or krypton. In one or more cycles between use of an adsorbent, regeneration of said adsorbent, and re-use of said adsorbent, the adsorbent need not be exposed to any gas including a substantial amount of an oxidizing agent (such as oxygen in air), a reducing agent (such as hydrogen), or both of the oxidizing and reducing agent. A "substantial amount" in this context may be anything that is greater than, or equal to, any of the foregoing percentages.

In most embodiments, the regeneration process first involves a cessation of introduction of hydrocarbon feedstock (e.g., aromatic hydrocarbon feedstock) into the adsorber. In many embodiments, the inert gas is then introduced into the adsorber. In many embodiments, introduction of inert gas replaces air, water, and/or hydrocarbon feedstock that have been introduced into, and are present within, the adsorber during the adsorption process. The inert gas comes into contact with the surfaces and pores of the zeolite.

In many embodiments of the present disclosure, the regeneration process is performed or carried out at a temperature of between approximately 100° C. and 300° C. In numerous embodiments, the regeneration process is performed at a temperature of between approximately 150° C. and 220° C. In selected embodiments, the regeneration process is performed at a temperature of between approximately 160° C. and 190° C. In most embodiments, the above-provided temperatures used for the regeneration process is maintained for between approximately 24 and 60 hours. In many embodiments, the above-provided temperatures used for the regeneration process is maintained for between approximately 24 and 36 hours.

As above-mentioned, the temperatures used for the regeneration processes provided by embodiments of the present disclosure are lower than the temperatures required with existing regeneration processes. The lower temperatures used in association with most embodiments of the present disclosure facilitate or enable increased safety of the regeneration process. In addition, less energy resources are required with the use of lower temperatures. Accordingly, the regeneration process provided by many embodiments of the present disclosure can be more cost-effective and/or environmentally friendly.

Subsequent the maintenance of the above-provided temperatures for the regeneration process for between approximately 24 and 60 hours or between approximately 24 and 48 hours, the temperature within the adsorber can then be reduced to approximately room temperature, for example approximately between 20° C. and 40° C.

The regeneration process provided by embodiments of the present disclosure enables a restoration or regeneration of function, structure, and/or reactivity of spent zeolites to that of fresh or regenerated zeolites. The use of inert gas as an agent for regeneration according to most embodiments of the present disclosure is possible because the adsorption process does not cause formation of heavy atoms of hydrocarbons as by-products. Accordingly, processes for removal or separating such heavy atoms of hydrocarbons are not required with the present disclosure. Instead, the adsorption process of most embodiments of the present disclosure produces contaminant adsorbates, for example unsaturated hydrocarbons adsorbates, which are adsorbed onto the surface, and more specifically within the pores, of the zeolite. In most embodiments, said unsaturated hydrocarbons adsorbates can be detached from the surface or pores of the zeolite without the need for high temperatures and/or complex removal or separation processes.

Regeneration of a spent zeolite can increase its performance back to at least approximately 50%, 60%, 70%, 80%, 90%, or 95% (or even at least any of approximately 98%, 99%, or 100%) of the performance of the fresh zeolite. For example, if a fresh zeolite reduced the bromine index (BI) of a hydrocarbon feedstock by at least 50%, then regeneration which results in increasing performance back to 90% of the performance of the fresh zeolite, would mean the regenerated zeolite is capable of reducing the bromine index (BI) of a hydrocarbon feedstock by 45% of the performance of the fresh zeolite.

Further Processing

Some embodiments may additionally include, after reducing the bromine index (BI), further processing, for example preparing a derivative of an aromatic compound, of the hydrocarbon feedstock. For example, para-xylene or other compounds may be prepared from the resulting feedstock (or from the further purified feedstock) by any of several methods known to a person of ordinary skill in the art. For instance, a process for producing alkenyl-aromatic hydrocarbon derivatives is disclosed by U.S. Pat. No. 4,689,436. In addition, a process for producing oxazole derivatives is disclosed by U.S. Pat. No. 5,962,685, and a process for preparing benzofuran derivatives is disclosed by U.S. Pat. No. 6,479,536. Furthermore, United States patent application of publication number US2008221362 (A1) teaches processes for producing optically active bis(alkynylphosphino) ethane-borane derivatives.

Adsorber or Adsorption System

Figure 1A:
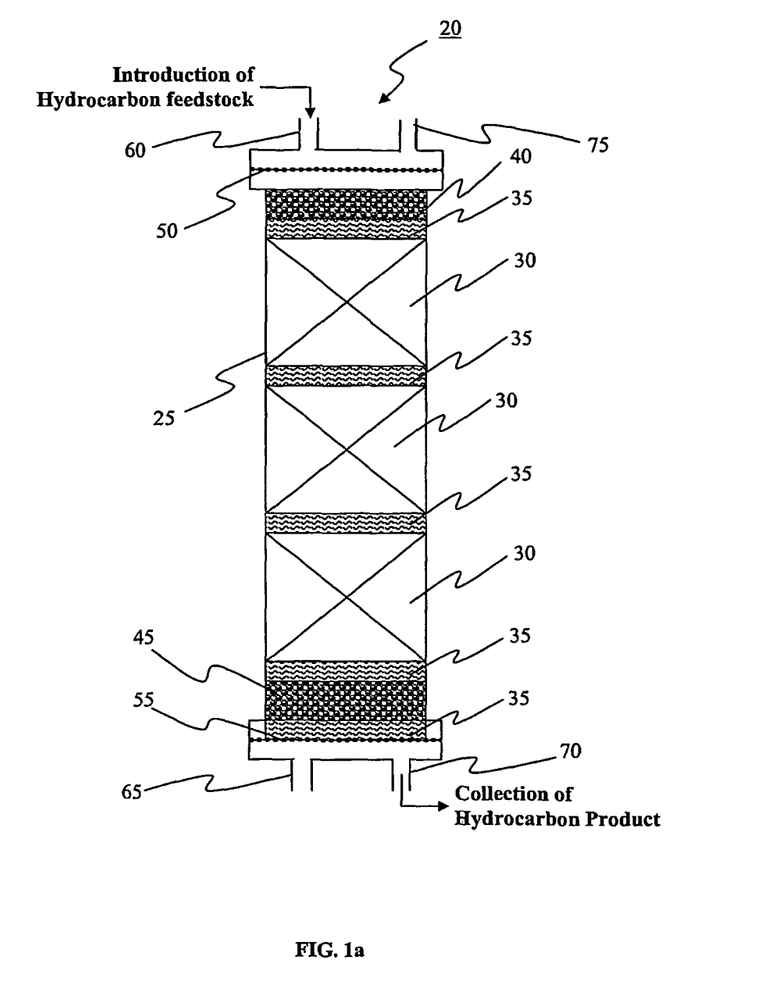
FIG. 1a is a partial cross-sectional illustration of an adsorption system or adsorber used for an adsorption process in accordance with an embodiment of the present disclosure.
Figure 1B:
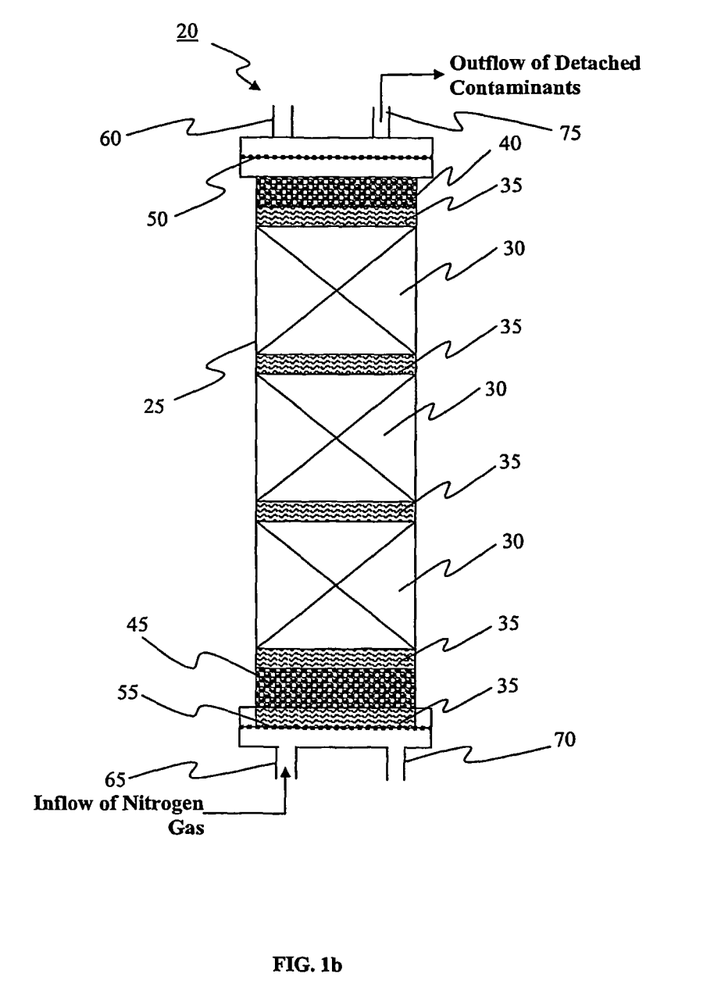
FIG. 1b is a partial cross-sectional illustration of an adsorption system or adsorber used for a regeneration process in accordance with an embodiment of the present disclosure.

An adsorber or adsorption system 20 is provided by some embodiments of the present disclosure, as shown in FIG. 1a and FIG. 1b. The adsorption system 20 can be used for facilitating, helping, or effectuating particular processes, or at least a portion of particular processes, provided by the present disclosure. For example, the adsorption system 20 can be used for adsorption processes provided by particular embodiments of the present disclosure. In addition, the adsorption system 20 can be used during regeneration processes provided by particular embodiments of the present disclosure.

In some embodiments, the adsorption system is a pilot slip stream adsorber. In many embodiments, the adsorption system 20 includes a body 25 (also known as a containing structure or housing). In some embodiments, the adsorption system 20 includes receiving structures 30 for receiving an adsorbent. The receiving structures 30 are carried within the body 25 of the adsorption system 20. In several embodiments, the adsorbent is the adsorbent as described above, and includes the zeolite that is described above. In numerous embodiments, the receiving structures 30 are shaped and dimensioned to receive the adsorbent and/or to secure the adsorbent thereto, thereonto, or therewithin.

In numerous embodiments, the adsorption system 20 includes a number of glass wool portions 35. In many embodiments, the glass wool portions 35 are portions that include glass wool. Glass wool is an insulating material that is made from fiberglass. Glass wool is typically arranged into a textile similar to wool. In some embodiments, the glass wool portions include other types of insulating material instead of, or in addition to, glass wool.

In some embodiments, the glass wool portions 35 are disposed or positioned on each side of the receiving structures 30. In some embodiments, the body or housing 25 of the adsorption system 20 is a column-shaped structure, and includes a top section 40 and a bottom section 45 that each includes inert balls. The top section 40 is disposed at a top part of the body 25 and the bottom section 45 is disposed at a bottom part of the body 25 as shown in FIG. 1a and FIG. 1b.

In addition, in several embodiments, the adsorption system 20 includes a top mesh 50 disposed at a top part of the body 25, and a bottom mesh 55 disposed at a bottom part of the body 25. In some embodiments, the top and bottom meshes 50 and 55 functions as a sieve for effecting selective passage of material therethrough.

In several embodiments, the adsorption system 20 includes at least one inlet (e.g., a feedstock inlet 60) carried by the body 25 through which the hydrocarbon feedstock, aromatic hydrocarbon feedstock, and/or the adsorbent can be introduced into the body 25. The feedstock inlet 60 is positioned at a top of the body 25. The introduction of hydrocarbon feedstock into the body 25 occurs during use of the adsorption system 20 for the adsorption process of particular embodiments of the present disclosure, as illustrated in FIG. 1a.

In many embodiments, the adsorption system 20 includes a gas inlet 65 that is shaped and dimensioned for mediating introduction of the inert or substantially unreactive gas (e.g., inert gas), such as that described above, into the body 25 of the adsorption system 20. In numerous embodiments, the gas inlet 65 is placed at a bottom part of the body 25. In selected embodiments, the gas inlet 65 is shaped, dimensioned, and/or configured for controlling the introduction of the inert or substantially unreactive gas. For example, the gas inlet 65 can be shaped, dimensioned, and/or configured for controlling at least one of rate, temperature, volume, and pressure of the inert or substantially unreactive gas that is being introduced into the body 25 of the adsorption system 20.

In some embodiments, the adsorption system 20 includes at least one product outlet 70 carried by the body 25 through which the hydrocarbon product can exit the body 25. In several embodiments, the product outlet 70 is disposed at a bottom part of the body 25. In some embodiments, the adsorption system 20 includes at least one contaminant outlet 75 carried by the body 25 through which the contaminants (e.g., unsaturated hydrocarbons such as olefins) can exit, and be removed from, the body 25. For example, when the adsorption system 20 is being used for the regeneration process as provided by particular embodiments of the present disclosure, the contaminants detached from the adsorbent can exit the body 25 via the at least one contaminant outlet 75. In several embodiments, the contaminant outlet 75 is disposed at a top part of the body 25.

In various embodiments, the adsorption system 20 further includes a controller (not shown) that can be programmed (e.g., the controller can run a software program) for controlling at least one rate, temperature, volume, and pressure of the inert or substantially unreactive gas being introduced into the body 25 of the adsorption system 20. The controller can be coupled to the gas inlet 65. In selected embodiments, the controller can be programmed for controlling a temperature or pressure within the body 25 of the adsorption system 20.

Representative examples of processes or methods for reducing the bromine index (BI) of aromatic hydrocarbon feedstocks according to particular embodiments of the present disclosure are provided in the following disclosure. Although representative examples are described below, a person of ordinary skill in the art will understand that modifications, variations, and/or adaptations can be made to the examples within the scope of the present disclosure.

EXAMPLE ONE

Figure 2:
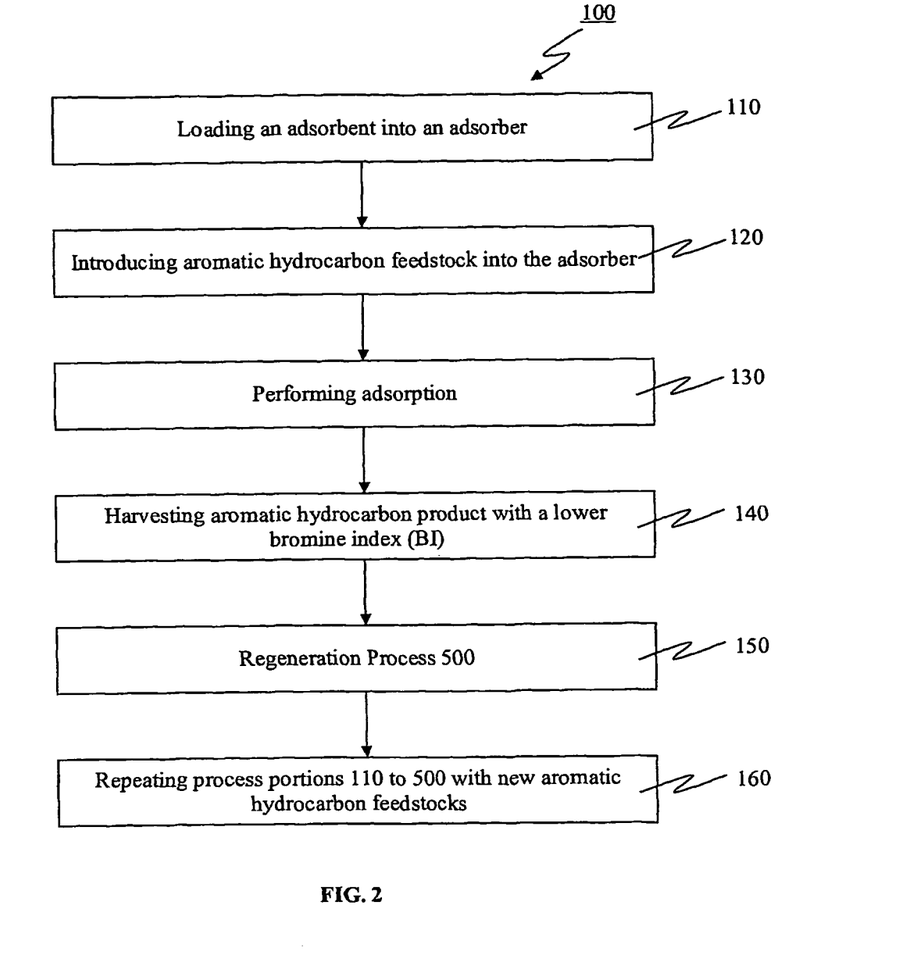
FIG. 2 is a flowchart of a process for reducing the bromine index (BI) of a hydrocarbon feedstock according to an embodiment of the present disclosure.

A process 100 for reducing the bromine index (BI) of an aromatic hydrocarbon, an aromatic hydrocarbon feedstock, or an aromatic hydrocarbon feedstream is provided according to an embodiment of the present disclosure. A flowchart of the process 100 is shown in FIG. 2.

In a first process portion 110, an adsorbent is loaded into an adsorber or adsorbing column. The adsorbent includes a ZSM-5 zeolite (structure type MFI) having pores of a pore size of between approximately 4 Å and 8 Å. In addition, the zeolite has a Si/Al of between approximately 1 and 150. The adsorbent had a surface area of about 425 m²/gram and a Na$_2$O weight percent of about 0.05 wt %.

In a second process portion 120, the aromatic hydrocarbon feedstock is introduced into the adsorber. The aromatic hydrocarbon feedstock has a bromine index (BI) of less than approximately 100 (i.e., 100 mg of bromine-reactive contaminants/100 g of aromatic hydrocarbon feedstock). The bromine index (BI) reflects the amount of bromine-reactive contaminants, for example unsaturated hydrocarbons, present in the aromatic hydrocarbon feedstock.

In a third process portion 130, an adsorption process (e.g., liquid phase adsorption process) is performed or carried out. The adsorption process involves physical contact between the aromatic hydrocarbon feedstock and the adsorbent, more specifically the zeolite.

As above described, the zeolite functions as a molecular sieve. The zeolite used with the process 100 of example 1 is a ZSM-5 zeolite selected for its particular morphology, porosity, pore size, pore size distribution, and/or surface properties. More specifically, the zeolite is selected for facilitating or allowing selective entry of the only the unsaturated hydrocarbons into the pores of the zeolite. In other words, the zeolite selectively adsorbs unsaturated hydrocarbons of the aromatic hydrocarbon feedstock that comes into contact therewith.

The adsorption process is performed at a set of conditions (e.g., pressure, temperature, and weight hourly space velocity (WHSV)) selected for facilitating or enabling the adsorption of the unsaturated hydrocarbons within the pores of the zeolite. More specifically, the adsorption process is performed at a pressure of between approximately 20 bar and 40 bar, a temperature of between 25° C. and 100° C., and a WHSV of between approximately 0.1 hr$^{-1}$ and 200 hr$^{-1}$.

The process performed in the process portion 130 of the process 100 results in adsorption of contaminants such as unsaturated hydrocarbons within the pores of the zeolite. Accordingly, the adsorption process performed in the process portion 130 of example one facilitates or effectuates removal of contaminants such as unsaturated hydrocarbons from the aromatic hydrocarbon feedstock. The removal of unsaturated hydrocarbons from the aromatic hydrocarbon feedstock results in a corresponding decrease in the bromine index (BI) of the aromatic hydrocarbon product that is produced from the aromatic hydrocarbon feedstock. This is to say the performance of the adsorption process facilitates or effectuates the production of aromatic hydrocarbon products with a bromine index (BI) lower than that of provided aromatic hydrocarbon feedstocks.

In a fourth process 140, the aromatic hydrocarbon product is harvested or collected from the adsorber or adsorption column. The collection of the aromatic hydrocarbon product can be done using methods, processes, or techniques known to a person of ordinary skill in the art.

As described above, the adsorption of contaminants such as unsaturated hydrocarbons within the pores of the zeolite results in the zeolite being spent (i.e., producing a "spent zeolite" or "spent adsorber"). This means the zeolite has an altered structure, and loses at least a portion of its function (e.g., adsorption capabilities).

In a fifth process portion 150, a regeneration process 500 is performed for regenerating the spent zeolite for producing a fresh zeolite. In other words, the regeneration process facilitates or effectuates a restoration or regeneration of the original or substantially original (i.e., a state prior to contact with the aromatic hydrocarbon feedstock) function, structure, and/or reactivity for the spent zeolite.

Figure 3:
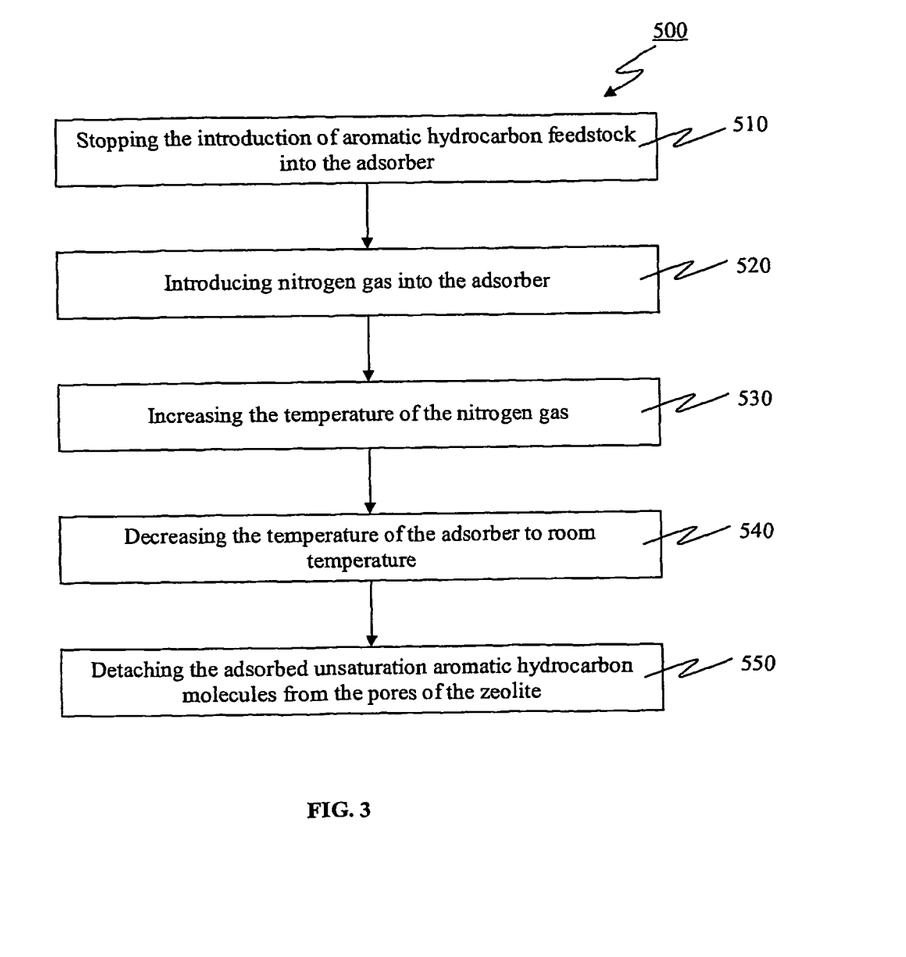
FIG. 3 is a flowchart of a regeneration process for producing a fresh zeolite, the regeneration process being performed during the process of FIG. 2.

A flowchart of the regeneration process 500 provided by example one of the present disclosure is shown in FIG. 3.

In a first process portion 510 of the regeneration process 500, the introduction of aromatic hydrocarbon feedstock into the adsorber is stopped or ceased. After stopping the introduction of aromatic hydrocarbon feedstock into the adsorber, nitrogen gas is introduced into the adsorber in a second process portion 520. The nitrogen gas introduced into the adsorber substantially replaces air, water, and aromatic hydrocarbon feedstock within the adsorber.

In a third process portion 530, the temperature of the nitrogen gas within the adsorber is increased to between approximately 150° C. and 220° C. The introduction of nitrogen gas at the temperature of between approximately 150° C. and 220° C. occurs for a time period of between approximately 24 hours and 36 hours.

After the time period of between approximately 24 hours and 36 hours, the temperature within the adsorber is then decreased in a fourth process portion 540. More specifically, the temperature within the adsorber is decreased to approximately room temperature, for example between approximately 20° C. and 35° C.

The regeneration process results in detaching or removal of the adsorbed unsaturated hydrocarbon (or adsorbed unsaturated hydrocarbon molecules) from the pores of the spent zeolite in a fifth process portion 550. The detachment or removal of unsaturated hydrocarbon from the pores of the spent zeolite results in regeneration of the spent zeolite to thereby produce a fresh or regenerated zeolite.

In a sixth process portion 160 of the method 100, the process portions 120 to 150 can be repeated using additional aromatic hydrocarbon feedstocks. Accordingly, the process 100 provided by example one of the present disclosure allows continual removal of contaminants (e.g., unsaturated hydrocarbons), and hence reduction of the bromine index (BI), of multiple aromatic hydrocarbon feedstocks via a continual regeneration of the zeolite (or adsorbent).

EXAMPLE TWO

Figure 4:
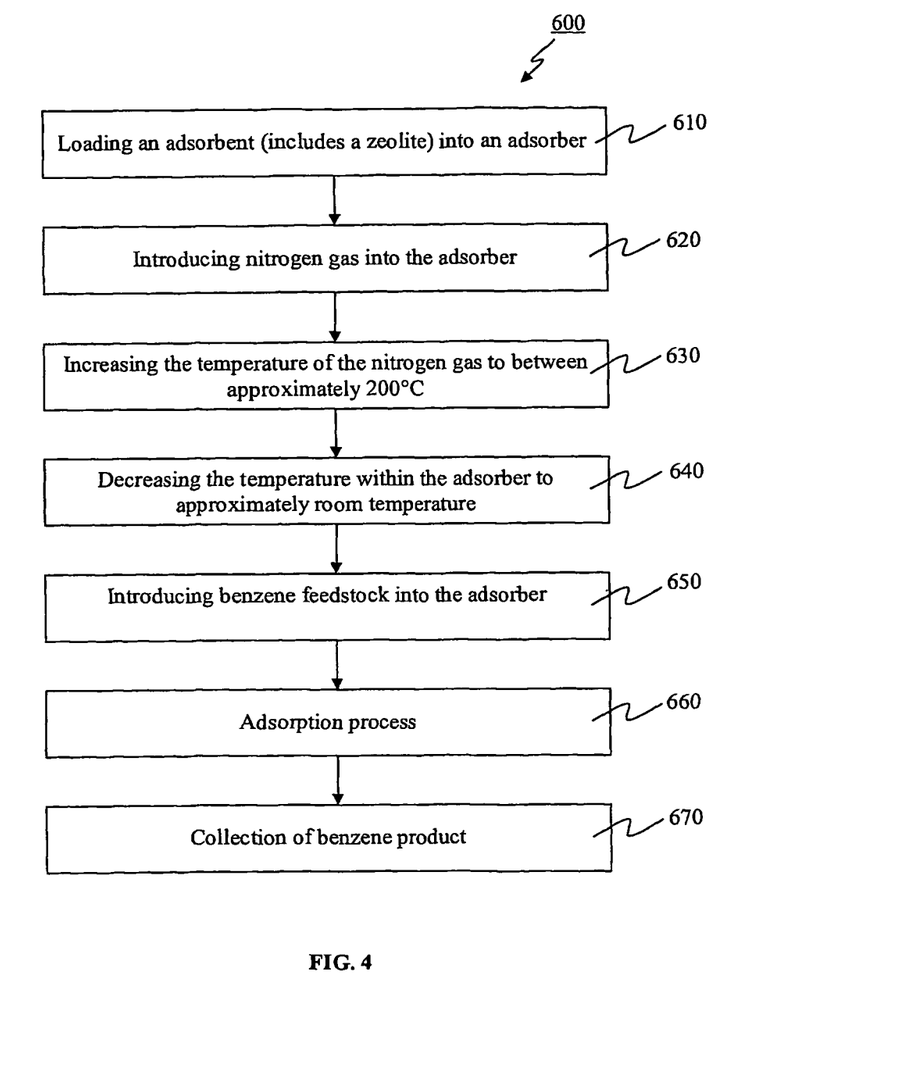
FIG. 4 is a flowchart of a process for reducing the bromine index (BI) of a benzene feedstock according to another embodiment of the present disclosure.

A process 600 for reducing the bromine index (BI) of an aromatic hydrocarbon feedstock, more specifically a benzene feedstock, is provided according to an embodiment of the present disclosure. A flowchart of the process 600 is shown in FIG. 4.

In a first process portion 610, an adsorbent, more specifically an adsorbent including one kilograms of ZSM-5 zeolite having an SiO2/Al2O3 ratio of about 23, a surface area of about 425 m²/gram, and an Na$_2$O weight % of about 0.05 is loaded into an adsorber or adsorption system (e.g., the adsorption system that is provided by particular embodiments of the present disclosure).

In a second process portion 620, nitrogen gas is introduced into the adsorber. The temperature of the nitrogen gas is then increased to approximately 200° C. in a third process portion 630. The nitrogen gas within the adsorber is maintained at approximately 200° C. for approximately 24 hours. After the 24 hour time period, the temperature of the nitrogen gas is then reduced to approximately room temperature in a fourth process portion 640.

In many embodiments, the second process portion 620 to the fourth process portion 640 ensures that the adsorbent, more specifically the zeolite, used for subsequent process portions of the process 600 is a fresh or regenerated zeolite. In other words, the second process portion 620 to the fourth process portion 640 represent at least part of a regeneration process for ensuring that the zeolite has free pores (i.e., pores that do not contain contaminants such as unsaturated hydrocarbons adsorbed therewithin) that are capable of receiving and adsorbing contaminants such as unsaturated hydrocarbons therewithin.

In a fifth process portion 650, an aromatic hydrocarbon feedstock is introduced into the adsorber. More specifically, a benzene feedstock is introduced into the adsorber in the fifth process portion 650. The benzene feedstock that is introduced into the adsorber in the fifth process portion 650 has characteristics and/or properties (e.g., purity and the bromine index (BI)) as summarized in a second column of Table A provided below. For instance, the benzene feedstock introduced into adsorber in the fifth process portion 650 has a purity of by weight of approximately 99.97%, a bromine index (BI) of between approximately 7 and 13, an oxygenate content of approximately 100 ppm and 200 ppm, and a nitrogen compound content of approximately 100 ppb.

The introduction of the benzene feedstock into the adsorber brings the benzene feedstock into contact with the adsorbent, which includes the zeolite, for facilitating or effectuating adsorption (e.g., liquid phase adsorption) in a sixth process portion 660. Conditions (e.g., pressure, temperature, and WHSV conditions) for the introduction of the benzene feedstock can be selected for facilitating or effectuating adsorption. For instance, the benzene feedstock is introduced into the adsorber with a feed rate of between approximately 5 kg/hr and 80 kg/hr at room temperature. In addition, the benzene feedstock is introduced into the adsorber at a pressure of between approximately 5 bar and 20 bar. Furthermore, the benzene feedstock is introduced into the adsorber at a WHSV of approximately 6 $hr^{-1}$.

During the adsorption process, contaminants such as unsaturated hydrocarbons are adsorbed onto the surfaces, more specifically within the pores, of the zeolite. This results in production of a benzene product with a lower bromine index (BI) than the benzene feedstock.

The bromine index (BI) of the benzene product obtained via the adsorption process can be determined. More specifically, a sample of the benzene product is analyzed to determine the properties and/or characteristics of the benzene product. The properties and/or characteristics of benzene product are summarized in the third column of Table A provided below.

As shown in the Table A below, the bromine index (BI) of the benzene product is between approximately 0 and 3. This reflects a percentage decrease in bromine index (BI) of the benzene product as compared to the benzene feedstock of between approximately 57% and 100%. The reduction of the bromine index (BI) of the benzene product reflects a removal of bromine-reactive contaminants, for example unsaturated hydrocarbons, from the benzene feedstock.

In addition, results of the analysis of the properties and/or characteristics of the benzene product indicate that the oxygenate content and the nitrogen compound content of the benzene product is less than the oxygenate content and the nitrogen compound content of the benzene feedstock. More specifically, the benzene product includes between approximately 10 ppm and 100 ppm of oxygenate, and between approximately 0 ppb and 10 ppb of nitrogen compound.

In addition, analysis or experiments were conducted to determine whether by-products were formed during the process 600. More specifically, gas chromatography was performed to determine whether by-products (e.g., heavy atom hydrocarbons such as hydrocarbons with at least six carbon-atoms) were formed during the process 600. Use of gas chromatography indicated that no by-products were formed during the process 600 of example two.

The absence of by-products (e.g., heavy atom hydrocarbons) formed with the process 600 provided by embodiments of the present disclosure removes a need for carrying out by-product separation and removal processes. Accordingly, the absence of by-products (e.g., heavy atom hydrocarbons) formed with the process 600 increases the efficiency and cost-effectiveness of the process 600 provided by embodiments of the present disclosure.

In a seventh process portion 670, the benzene product is collected or harvested. The collection of the benzene product can be done using methods, process, or techniques known to a person of ordinary skill in the art. The lower bromine index (BI) of the benzene product as compared to the benzene feedstock reduces the likelihood of occurrences of undesired side reactions when the benzene product is subsequently utilized or processed (e.g., in downstream processes).

TABLE A

Properties of Benzene Feedstock and Benzene Product

| Properties | Benzene Feedstock (Inlet) | Benzene Product (Outlet) |
| --- | --- | --- |
| Purity (wt %) | 99.97 | 99.98 |
| BI (mg-Br/100 g-sample) | 10-20 | 0-3 |
| Oxygenate (ppm) | 100-200 | 10-100 |
| Nitrogen compound (ppb) | 100 | 0-10 |
| WSHV ($hr^{-1}$) | 6 | — |

EXAMPLE THREE

Example three illustrates in further detail the reduction of the bromine index (BI) of an aromatic hydrocarbon feedstock, more specifically a benzene feedstock, in accordance with embodiments described herein. In this example, the results of gas chromatography conducted on a benzene product resulting from contacting a benzene feedstock with a zeolite adsorbent in accordance with disclosed embodiments are presented. Lab scale adsorptions of this example were performed in a glassware system. 20 g of adsorbent sample in the form of a ZSM-5 zeolite having an $SiO_2/Al_2O_3$ ratio of about 23, a surface area of about 425 m2/g, and an $Na_2O$ weight % of about 0.05 wt % was heated in an oven at a temperature 180 C overnight to remove traces of water. The glassware system included a cylinder having plastic valve at the bottom for controlling the contact time between benzene feedstock and the adsorbent. Glass wool was first packed as a layer on the top of the plastic valve to help retain the small adsorbent particles in the cylinder. The heated adsorbent was removed from the 180 C oven and immediately packed into the glassware cylinder on the top of the glass wool. Next a thick layer of glass wool was packed onto the heated adsorbent in order to increase benzene feedstock flow distribution across the adsorbent. The top of the cylinder was provided with a fitting to receive benzene feedstock samples fed to the top of the glass cylinder above the thick layer of glass wool. Benzene-containing gas collected from the bottom of the cylinder was directed to a gas chromatograph described below where the composition of the collected gas was determined. The gas chromatograph was also used to determine the composition of the benzene feedstock prior to its contact with the adsorbent. The adsorption was carried out at room temperature, pressure of ~8 bars, and a WHSV of 12 $hr^{-1}$.

tacting with the adsorbent. Every peak of the chromatograms is listed in the Table B below. The results show that all unknown samples (denoted X1-X13) were substantially removed from the benzene feedstock, resulting in benzene-containing product having a higher benzene purity coinciding with the reduction or disappearance of BI value (BI=0). Although X1-X13 were unknown samples, it was confirmed by NMR that X1-X13 were unsaturated hydrocarbon; i.e., BI contributors or olefin.

In term of by-product formation, the results of the gas chromatography produced no evidence of the formation of by-products, thus indicating that embodiments of the present disclosure are able to reduce the BI without formation of by-products.

TABLE B

Results of GC Analysis of Benzene Feedstock and Benzene-containing Product

| Component | Benzene sample 1 Inlet | Benzene sample 1 Outlet | Benzene sample 2 Inlet | Benzene sample 2 Outlet | Benzene sample 3 Inlet | Benzene sample 3 Outlet |
|---|---|---|---|---|---|---|
| BI Value | 10.42 | 0 | 11.02 | 0 | 12.83 | 0 |
| X1 | 0.001212 | | | | | |
| Pentane | 0.001003 | 0.001803 | | | | |
| Cyclopentane | 0.001106 | 0.002106 | | | | |
| n-Hexane | 0.000722 | 0.000822 | | | | |
| Methylcyclopentane | | | | | | |
| Benzene | 99.931684 | 99.9447 | 99.9275 | 99.9417 | 99.9063 | 99.9300 |
| Cyclohexane | 0.0046 | 0.0056 | 0.0057 | 0.0068 | 0.0071 | 0.0011 |
| X2 | | | | | | |
| X3 | 0.003944 | | 0.004518 | | | |
| X4 | 0.001183 | | 0.0014 | | 0.0019 | |
| X5 | 0.001408 | | 0.0019 | | 0.0024 | |
| 2-Methylhexane | | | | | | |
| 3-Methylhexane | | | | | | |
| X6 | | | | | | |
| 2,2,4-Trimethylpentane | 0.002673 | 0.001948 | 0.0032 | 0.0054 | 0.0039 | 0.006 |
| n-Heptane | 0.000868 | 0.000868 | 0.000619 | 0.000519 | 0.0011 | 0.0021 |
| X7 | 0.000809 | | 0.0008 | | 0.0009 | |
| X8 | 0.006593 | | 0.008739 | | 0.0096 | |
| Methylcyclohexane | 0.031809 | 0.039309 | 0.0361 | | 0.0355 | 0.0365 |
| X9 | 0.00757 | | 0.0096 | 0.0455 | 0.0097 | |
| X10 | | | | | | |
| Toluene | 0.002809 | 0.00276 | | | 0.0025 | 0.0025 |
| Ethylbenzene | | | | | 0.000762 | 0.000862 |
| n-Propylbenzene | | | | | 0.000635 | 0.00335 |
| n-Decane | | | | | | |
| 1,2,3-Trimethylbenzene | | | | | 0.00152 | 0.00285 |
| t-Decalin | | | | | 0.000628 | 0.000868 |
| n-Undecane | | | | | 0.009969 | 0.00273 |
| 1,2,4,5-Tetramethylbenzene | | | | | 0.000754 | 0.000973 |
| X11 | | | | | 0.000716 | |
| X12 | | | | | 0.000614 | |
| X13 | | | | | 0.001364 | |
| n-Dodecane | | | | | 0.016962 | 0.010094 |

| Gas Chromatograph measurement | |
|---|---|
| Features | Type/value |
| GC-FID | Shimadzu 2014 |
| Column | RT-Q-Plot |
| Feed pre-heater temperature | 80 C. |
| Injector temperature | 100 C. |
| Column temp | 80-120 C. |
| Carrier gas type | N2 |
| Carrier gas flow rate | 5 ml/min |
| Detector temperature | 150 C. |

Table B below lists the composition of the benzene feedstock and the composition of the feedstock after con- As described above, embodiments of the present disclosure provide processes for reducing the bromine index (BI) of hydrocarbon feedstocks or aromatic hydrocarbon feedstocks. In most embodiments, adsorption (e.g., liquid phase adsorption) is performed for adsorbing contaminants (e.g., unsaturated hydrocarbons) present in the hydrocarbon feedstocks within the pores of provided zeolite (or adsorbent). In accordance with many embodiments, the adsorption can be performed at relatively low temperatures, for example between 25° C. and 100° C., and pressures. The use of said relatively lower temperatures and pressures reduces energy consumption and enhances cost-effectiveness. In addition, no by-products, more specifically no heavy atom hydrocarbons, are formed in association with many embodiments, thereby removing a need for performance of by-product removal or separation processes. In addition, with many embodiments of the present disclosure, there is no need for performing rejuvenating processes as is required with many existing processes for reducing bromine index (BI) of hydrocarbons. Furthermore, in many embodiments, spent zeolites can be regenerated as desired by using nitrogen gas. The regeneration process provided by many embodiments of the present disclosure removes the need for continual replacement of spent zeolites with new and fresh zeolites, thereby enabling cost-savings for a user of particular processes of the present disclosure.

Aspects of particular embodiments of the disclosure addresses one or more problems or disadvantages associated with conventional methods, processes, techniques, systems, devices, and components used for reducing the bromine index of hydrocarbon feedstocks, or provide alternative processes. While advantages associated with certain embodiments have been described in the disclosure, other embodiments may also exhibit such advantages, and not all embodiments need necessarily exhibit such advantages to fall within the scope of the disclosure. It will be appreciated by a person of ordinary skill in the art that several of the above-disclosed methods, processes, or systems, and features, aspects, or alternatives thereof, may be desirably combined into other different methods, processes, systems, or applications. In addition, various modifications, alterations, and/or improvements may be made to various embodiments that are disclosed by a person of ordinary skill in the art within the scope and spirit of the present disclosure.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process for reducing the bromine index (BI) of a hydrocarbon feedstock, the process comprising contacting the hydrocarbon feedstock with an adsorbent comprising a zeolite with a pore size of between approximately 4 Å and 8 Å in an adsorption process so as to reduce the bromine index (BI) of the hydrocarbon feedstock, wherein all the reduction in the bromine index (BI) of the hydrocarbon feedstock is attributable to adsorption of contaminants on the zeolite without chemical modification of the contaminants.

2. The process as in claim 1, further comprising contacting the adsorbent which has been contacted with the hydrocarbon feedstock with a substantially inert gas.

3. The process as in claim 2, wherein the substantially inert gas is at least approximately 70% nitrogen gas by volume, and contacting the adsorbent, which has been contacted with the hydrocarbon feedstock, with the substantially inert gas removes contaminants which are adsorbed within the pores of the zeolite, the contaminants being from the hydrocarbon feedstock.

4. The process as in claim 3, wherein the removal of the contaminants from the pores of the zeolite produces a regenerated zeolite.

5. The process as in claim 3, wherein the substantially inert gas is at a temperature of approximately between 150° C. and 300° C.

6. The process as in claim 5, wherein the substantially inert gas is at a temperature of approximately between 190° C. and 200° C.

7. The process as in claim 1, wherein the zeolite has a pore size of between approximately 5 Å and 7 Å.

8. The process as in claim 7, wherein the zeolite comprises at least one zeolite structure type of MFI, MEL, MRE, MTW, EUO, MTT, MFS, AEL, AFP, HEU, FER, TON, and any combination thereof.

9. The process as in claim 8, wherein the zeolite comprises at least one zeolite structure type of MFI.

10. The process as in claim 7, wherein the zeolite has a Si / Al ratio of between approximately 1 and 150.

11. The process as in claim 10, wherein the zeolite has a Si / Al ratio of between 2 and 100.

12. The process as in claim 1, wherein the adsorption process is performed at a temperature of between approximately 25° C. and 100° C.

13. The process as in claim 12, wherein the adsorption process is performed at a temperature of between approximately 25° C. and 60° C.

14. The process as in claim 12, wherein the adsorption process is performed at a pressure of between approximately 1 bar and 50 bar.

15. The process as in claim 14, wherein the adsorption process is performed at a pressure of between approximately 20 bar and 40 bar.

16. The process as in claim 14, wherein the adsorption process is performed at a weight hourly space velocity (WHSV) of between approximately 0.01 $hr^{-1}$ and 200 $hr^{-1}$.

17. The process as in claim 16, wherein the hydrocarbon feedstock is an aromatic hydrocarbon feedstock, and the contaminants comprise unsaturated hydrocarbons.

18. The process as in claim 17, wherein the reduction in the bromine index (BI) of the aromatic hydrocarbon feedstock is between approximately 50% and 100%.

19. The process as in claim 17, further comprising, after the adsorption process, processing of the aromatic hydrocarbon feedstock to prepare a derivative of the aromatic hydrocarbon feedstock.

20. The process of claim 1, wherein contacting the hydrocarbon feedstock with an adsorbent further comprises contacting the hydrocarbon feedstock with an adsorbent at a temperature ranging from about 10° C. to about 120° C.

21. The process of claim 20, wherein contacting the hydrocarbon feedstock with an adsorbent further comprises contacting the hydrocarbon feedstock with an adsorbent at a pressure ranging from about 0.5 bar to about 100 bar.

22. The process of claim 1, wherein contacting the hydrocarbon feedstock with an adsorbent further comprises contacting the hydrocarbon feedstock with an adsorbent at a pressure ranging from about 0.5 bar to about 100 bar.

23. The process of claim 1, wherein contacting the hydrocarbon feedstock with an adsorbent further comprises contacting the hydrocarbon feedstock with an adsorbent at a weight hourly space velocity (WHSV) ranging from about 0.01 to about 250 $hour^{-1}$.

24. The process of claim 1, wherein the BI of the hydrocarbon feedstock is less than 500.

25. The process of claim 1, further comprising controlling the temperature at which the hydrocarbon feedstock is contacted with the adsorbent to a value whereby the contaminants are adsorbed on the adsorbent without chemical modification of the contaminants.

26. The process of claim 25, wherein the chemical modification involves an alkylation, polymerization, or oligomerization process.

27. The process of claim 26, further comprising controlling the pressure at which the hydrocarbon feedstock is contacted with the adsorbent to values whereby the contaminants are adsorbed on the adsorbent without chemical modification of the contaminants.

28. The process of claim 1, wherein the hydrocarbon feedstock includes an amount of an aromatic product and the adsorption process does not reduce the amount of the aromatic product in the hydrocarbon feedstock.

29. The process of claim 1, wherein the hydrocarbon feedstock before contacting the adsorbent contains an amount of an aromatic product and the amount of the aromatic product in the hydrocarbon feedstock after the hydrocarbon feedstock contacts the adsorbent is substantially equal to the amount of the aromatic product present in the hydrocarbon feedstock before the hydrocarbon feedstock contacts the adsorbent.

30. The process of claim 1, wherein the chemical modification of the contaminants includes reacting the contaminants with an aromatic product in the hydrocarbon feedstock.

31. The process of claim 30, wherein the aromatic product is benzene.

32. The process of claim 1, wherein the hydrocarbon feedstock after contacting the adsorbent is substantially free of by-products.

33. The process of claim 32, wherein the by-products result from a chemical reaction between an aromatic product in the hydrocarbon feedstock and a contaminant in the hydrocarbon feedstock.

34. The process of claim 33, wherein the chemical reaction involves alkylation of the aromatic product with the contaminant.

* * * * *